United States Patent [19]
Christopher

[11] Patent Number: 5,379,791
[45] Date of Patent: Jan. 10, 1995

[54] DUAL-HEAD FLOW CONTROLLER AND METHOD

[76] Inventor: John F. Christopher, 1125 Coleman Rd., Roswell, Ga. 30075

[21] Appl. No.: 116,336

[22] Filed: Sep. 3, 1993

[51] Int. Cl.⁶ .............................................. G01N 15/06
[52] U.S. Cl. ................................... 137/1; 73/61.71; 137/593
[58] Field of Search ............... 137/1, 593; 73/61.42, 73/61.71

[56] References Cited

U.S. PATENT DOCUMENTS

| | | | |
|---|---|---|---|
| 2,523,634 | 9/1950 | Pyle | 137/593 |
| 4,317,539 | 3/1982 | Pollock | 137/593 X |
| 4,492,921 | 1/1985 | Sandulyak | 73/61.71 X |
| 5,211,677 | 5/1993 | Sargeant | 73/61.71 |

OTHER PUBLICATIONS

Model 211 Sensor Owners Manual (Preliminary), Oct. 1988, Met One, Inc., Grants Pass, Oreg.
"Your Greatest Liquid Assets", Met One, Inc. (undated).
Specification Sheet for Model 400 Flo-Controller, McMillan Company, 1991.

Primary Examiner—Robert G. Nilson
Attorney, Agent, or Firm—Kennedy & Kennedy

[57] ABSTRACT

A dual-head flow controller having a positive-head and a negative-head for supplying a sample fluid from a source to a restriction at a constant rate, with the magnitude of the negative head about the same as that of the positive head, independent of the pressure of the source fluid. A positive-head tube having a distal open end connects for fluid communication with the supply. The positive-head tube extends a first predetermined distance above a mean elevation of the restriction in the measuring chamber. A negative-head tube communicates fluid from the restriction to a distal open end. A portion of the negative-head tube extends downwardly a second distance below the mean elevation of the restriction. The fluid, being communicated in response to the combined head pressures, flows at a constant rate through the restriction, independent of changes in the pressure of the source fluid.

12 Claims, 2 Drawing Sheets

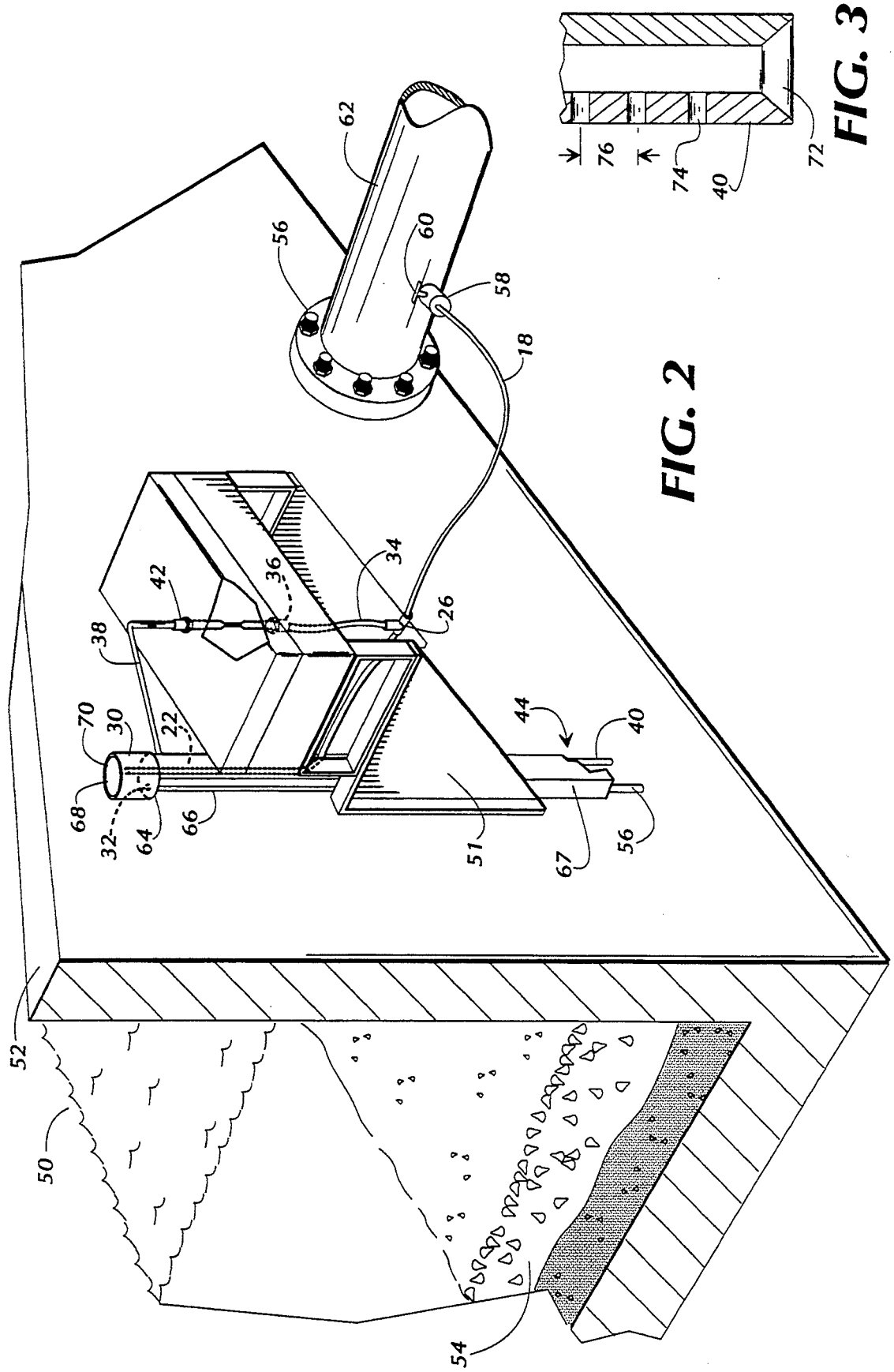

DUAL-HEAD FLOW CONTROLLER AND METHOD

TECHNICAL FIELD

The present invention relates to fluid flow controllers. More particularly, the present invention relates to a non-mechanical fluid flow controller for supplying fluid at a constant rate of flow to a restriction, and to a method therefor.

BACKGROUND OF THE INVENTION

Many municipal utility systems supply potable water to residents and business in the community for drinking, bathing, manufacturing, and the like. The potable water travels from a treatment plant through pipes known as water mains and branches to the homes and businesses. Water treatment facilities process water from rivers, lakes, and underground in order to supply potable water to the municipal water system. The processing at the treatment facility involves filtering the water to remove particles and microorganisms, adding chemicals to purify the water, and monitoring the quality of the water placed in the water distribution system. After use, waste water generally travels to a waste treatment facility through sewer pipes. The waste water is typically treated to remove wastes and to neutralize fluid contaminants before the water is discharged into lakes or rivers.

A typical water treatment facility for municipalities draws water from a source of fresh water, such as a river, a lake, or groundwater. The water typically moves through the treatment facility by gravity flow, so the water is first pumped to an elevated chemical treatment basin. One chemical alum forms flocs which are sticky globs of slit, bacteria, and other small particles. The water enters a settlement basin where the flocs settle to the bottom for collection. The water is then piped to a filter basin which typically has a layer of sand and gravel. Some filters may include a layer of activated charcoal. The filter collects the larger particles from the water. A reservoir holds the filtered water which receives a final chemical treatment before entering the distribution mains and branches.

Typically, the treatment facility has many settlement filter basins. Inlet manifolds distribute the water through separate pipes into the respective basin. Similarly, outlet manifolds collect the water from the respective basin for communicating the water to the next treatment basin.

The quality of the potable water provided to a municipal water system is carefully monitored. Quality concerns particularly include turbidity, microorganisms, and taste. Turbidity of the water involves the cloudiness caused by particles such as silt and microorganisms. Microorganisms can also cause illness to persons using the water. Disinfection with chemicals kills bacteria. Other processes, such as aeration, improve the taste and odor of the water.

Federal and state environmental legislation directs appropriate government agencies to establish and monitor water quality standards. These agencies set forth the criteria that water systems must meet to maintain government funding and to avoid fines for failing to meet the criteria. One measure of quality is the number and size of particles in the water. One test that water systems must report is the percentage of particles removed during filtration. Various devices have been developed to measure and report information about the number and size of particles in water. One of the devices receives and evaluates a sample of tile water entering the filter basin. Typically the sample is taken from the flow in the discharge pipe at the settlement basin. Another device receives and evaluates a sample of the water discharged from the filter basin. The results are compared to determine the percentage of particulate removed by the filter.

Typically, the particle measuring devices pass the sample of water through a narrow restriction. A supply tube first communicates water to the measuring device from a source such as the discharge pipe of the settlement or filter basin. Typically, a beam of light, such as a laser, is directed into the restriction. Particles in the sample flow deflect light energy from the laser source to a photosensitive device. The device evaluates the reflected light to determine size and concentrations of particles in the water. A microprocessor operatively connected with the measuring device records the concentrations and other relevant data about the nests. The test results can then be reported to appropriate personnel and monitoring agencies. Also, the municipal water company can use the test data to monitor and correct filtration problems.

Known devices measure the sample as a continuous flow and evaluate the flow over a brief period such a one minute. To determine the concentration of particles in the sample, the device must determine the volume in the sample. One device includes a turbine flow meter which determines the volume of water included in the sample being measured. This type of equipment however is expensive and complicated to maintain in the industrial environment of a water treatment facility.

Another known device evaluates water supplied at a constant flow rate. Typically, the water travels at 100 milliliters per minute for particle concentrations of less than 3,000 counts per minute. Heavier concentrations are more readily counted at a slower rate, for example, 50 milliliters per minute.

While the device using a constant flow rate is less expensive and meets the need for monitoring particulate matter in water, drawbacks limit its use. The significant problem is assuring that the proper flow rate of fluid is passing through the measuring chamber during the test. Errors in particle concentration can be made, if the flow rate actually is different from the expected flow rate. For example, a flow rate of 90 milliliters per minute will result in about a 10% error if the device computes particulate concentration based on a flow rate of 100 milliliters per minute. Flow rate can decrease as the pressure of the water being tested decreases. For devices attached to the outlet of the filter, the pressure can decrease over time. As the filter removes particles from the water, the back pressure of the filter increases. The filter becomes a load on the flow of the water through the filter.

An adjustable valve in the discharge tube of the measuring device compensates for the decrease in pressure of the sample fluid entering the measuring chamber. One such valve is an electronic flow controller. This device has a sensor such as a turbine wheel that determines the flow rate of the fluid. The sensor is operatively coupled to a servo valve which opens and closes in response to changes in the flow rate of the fluid entering the measuring chamber. A decrease in the pressure decreases the flow rate of the fluid. The servo valve then opens to allow greater flow through the discharge tube. Opening the discharge tube increases the flow rate of the fluid at the lower pressure so that the measuring chamber receives the expected flow rate of fluid.

Another device is a rotameter placed in-line with the discharge tubing from the measuring chamber to control the flow rate through the chamber. Typically, the rotameter is manually set for the desired flow rate. A float disk controls fluid flow through the rotameter and indicates the flow rate. When the pressure drops as discussed above, the flow rate decreases and the float disk in the valve lowers. The float disk can then be manually reset by turning a needle valve to re-establish the expected flow rate in the measuring chamber. The manually reset rotameter however requires a technician verify and adjust the meter each time the measuring device is to test a sample. Many treatment facilities would require a number of the measuring devices (two for each filter basin) that test samples once or twice per hour. A full-time technician may be required to conduct the tests.

Accordingly, there is a need in the art for an improved fluid flow controller and method for supplying a sample of a fluid to a restriction at a constant rate independent of the pressure of the fluid from which the sample is taken.

SUMMARY OF THE INVENTION

The present invention meets the need for an improved fluid flow controller and method that supplies a sample of fluid to a restriction at a constant rate independent of the pressure of the fluid from which the sample is taken. Generally described, the present invention provides a dual-head flow controller having a positive-head and a negative-head for supplying fluid to a restriction at a constant rate.

More particularly described, the present invention provides a supply tube for communicating a sample fluid from a supply to a restriction in a measuring chamber. A positive-head tube connects for fluid communication with the supply tube. The distal end of the positive-head tube is open. The positive-head tube extends a first predetermined distance above a mean elevation of the restriction in the measuring chamber for a pressure head having a first value. A negative-head tube communicates fluid from the restriction to a distal open end. A portion of the negative-head tube extends downwardly a second distance below the mean elevation of the restriction in the measuring chamber for a pressure head of a second value. It is preferred that the magnitudes of the heads be about the same. The fluid, being communicated under pressure to the restriction for measuring the particles in the fluid, flows at a constant rate, independent of changes in the pressure of the fluid to be sampled.

The supply tube, the positive-head tube, and the negative-head tube, which communicate the fluid, each preferably have a same cross-sectional width or diameter. The restriction has a cross-sectional width or diameter smaller than that for the tubes communicating the fluid. The dual-head flow controller described above can also include a catch basin that connects at a distal end of the positive-head tube for receiving fluid overflow. A drain in the catch basin allows the catch basin to empty.

The present invention further provides a method of supplying a constant rate flow of a fluid to a restriction in a measuring chamber for measuring particles in the fluid. Generally described, the method comprises communicating a fluid from a supply to a restriction in a measuring chamber, in response to a positive and negative head that combine to push and pull, respectively, the fluid through the restriction.

More particularly described, the method comprises communicating a fluid from a source supply to both a restriction in a measuring chamber and to a positive-head tube having a distal open end. The positive-head tube extends a first predetermined distance above a mean elevation of the restriction in the measuring chamber for a positive pressure head. The fluid discharges from the restriction through a discharge tube having a distal open end. A portion of the discharge tube extends downwardly a second distance below the mean elevation of the restriction in the measuring chamber for a negative pressure head. The magnitude of the negative head is preferably about the same as that of the positive head. The fluid, being communicated to the restriction for measuring the particles in the fluid, flows at a constant rate independent of the pressure of the source from which the fluid is taken.

Features and advantages of the present invention will become apparent from a reading of the following specification, in conjunction with the drawings and appended claims.

BRIEF DESCRIPTION OF THE DRAWINGS

FIG. 2 is a perspective view of a preferred embodiment of a dual-head flow controller according to the present invention operatively connected to a water treatment filter.

FIG. 3 is a cross-sectional view of a distal end of a tube that communicates fluid in the dual-head flow controller illustrated in FIG. 2.

DETAILED DESCRIPTION

Figure 1:
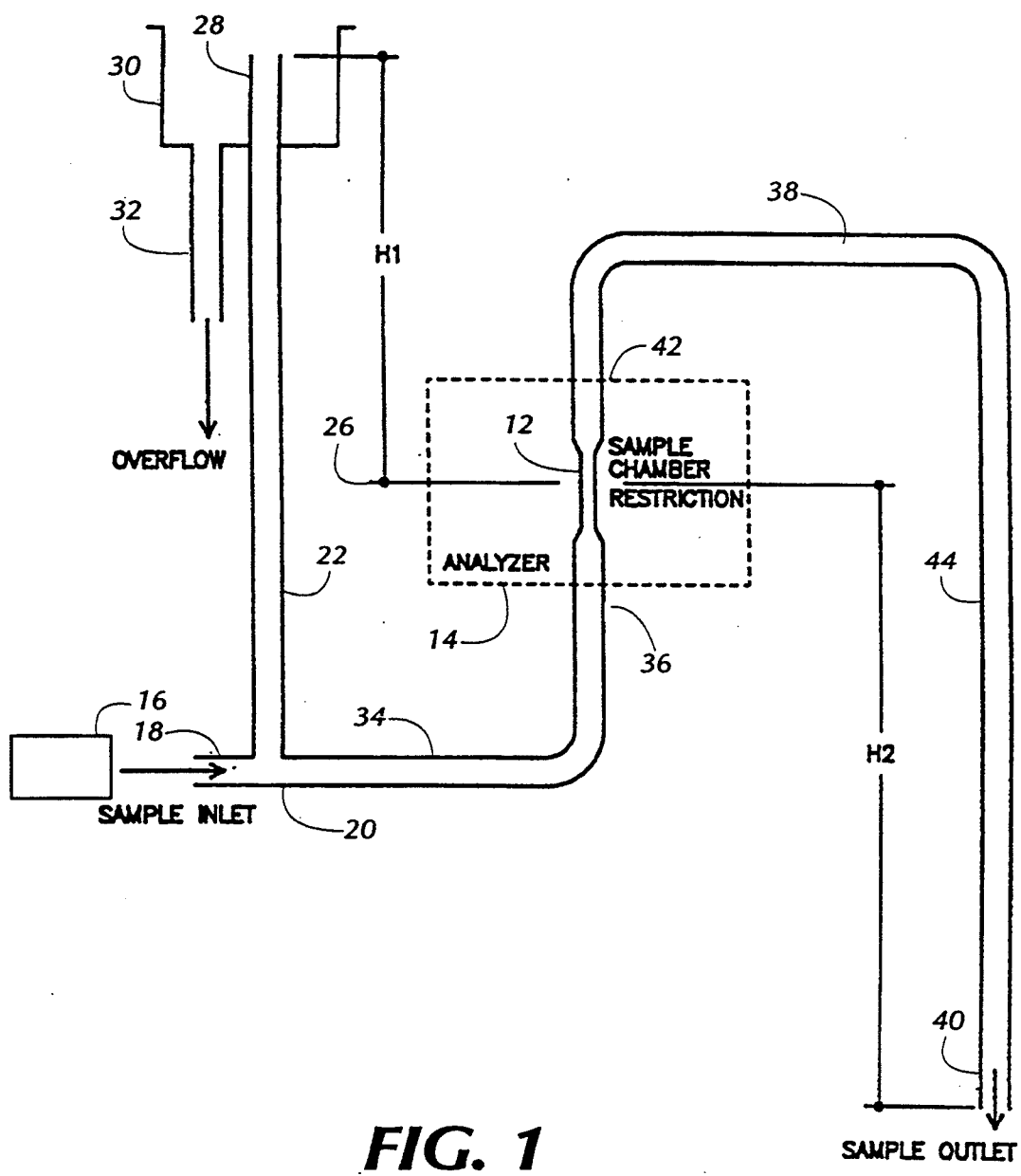
FIG. 1 is a schematic diagram of the dual-head flow controller of the present invention.

Referring now in more detail to the drawings, in which like numerals indicate like parts throughout the several views, FIG. 1 shows a schematic view of a dual-head flow controller 10 according to the present invention. The controller 10 provides a constant flow of a fluid, such as water, to a restriction 12 in a measuring device 14 that evaluates the fluid taken as a sample from a source supply generally designed 16. As discussed below, the flow rate of the fluid through the restriction is independent of the pressure of the source supply of fluid. The measuring device thus can be set for evaluating a constant volume of fluid.

A sampling supply tube 18 connects to the source supply 16 of the fluid. A tee-junction 20 having a first leg and a second leg connects to the sampling tube 18. A positive-head tube 22 connects to one leg of the tee-junction 20. The tube 22 extends upwardly a predetermined distance above a mean elevation 26 of the restriction 12 in the measuring device 14. A distal end 28 of the tube 22 is open. The tube 22 filled with the fluid creates a positive head H1. In the illustrated embodiment, the upper end of the tube 22 enters a catch basin 30 having an overflow drain 32. The catch basin 30 is open for communication with the atmosphere.

A fluid inlet tube B4 connects to the second leg of the tee-junction 20 and to an inlet 36 of the measuring device 14. A discharge tube 38 having an open distal end 40 connects to an outlet 42 of the measuring device 14. A portion 44 of the discharge tube 38 extends downwardly below the mean elevation 26 of the restriction 12 in the measuring device. The fluid that fills the portion 44 of the discharge tube 38 creates a negative head H2. The portion 44 is also referred to herein as the negative-head tube 44.

FIG. 2 illustrates a preferred embodiment of the dual-head flow controller 10 operatively connected to the measuring device 14 that counts particles in water discharged from a filter 50 in a water treatment plant. The measuring device 14 mounts with angle brackets 51 to a wall 52 of the filter 50 near a discharge 56 of the filter. The filter 50 is known as a declining head filter. Such filters have the wall 52 for holding water which seeps downward through a filter media generally designated 54 to the discharge 56. The discharge 56 is selectively opened or closed to control the outflow from the filter 50 (the valve to accomplish this is not illustrated). The filter media typically is layers of sand, activated charcoal, and gravel.

A junction 58 having a valve 60 connects the sampling tube 18 to a water main 62 at the discharge 56. The sampling tube 18 connects with the tee-junction 20 to the positive-head tube 22 and the inlet tube 36. The catch basin 30 at the upper end of the positive-head tube 22 in the illustrated embodiment is a two inch length of copper pipe having a one inch diameter. A cap 64 is soldered to the pipe to form a bottom. A drain tube 66 connects to the drain opening 32 in the cap 64. The drain tube 66 extends down below the measuring device for discharging overflow fluid from the positive-head tube 22; for example, water discharged onto the ground. The upper end of the positive-head tube 22 extends into the catch basin 30. A cap 68 loosely fits on the catch basin 30 as a cover. The cap 68 includes a hole 70 so the catch basin 30 and the distal end 28 of the tube 22 are open to atmospheric pressure.

In the illustrated embodiment, the fluid inlet tube 34 and the discharge tube 38 connect to the measuring device 14 with compression fittings. The discharge tube 38 extends towards the tube 22 and then downwardly parallel with the drain tube 66 so that the distal end 40 is below the mean elevation 26 of the restriction 12. An L-angle member 67 connects to one of the brackets 51 and extends parallel to the tubes 22, 44, and 66. The tubes connect to the member 67 for support. The L-angle member 67 is partially cut-away to better illustrate the tubes.

The tubes 18, 22, 34, and 38 carry the sample fluid through the flow controller 10. These tubes are generally referred to as the fluid communication tubes. FIG. 3 is a cross-sectional view of the distal end 40 of the discharge tube 38, which is representative of the fluid communication tubes. These tubes are preferably one-fourth inch copper tubing type L with a three-sixteenth inch inner diameter. The inner diameter of the restriction 12 is less than the inner diameter of the tubes 18, 22, 34, and 38. The tubes are cut to length using a carbide saw. The distal ends of the tubes are then bored with a countersink drill to form a positive bevel 72 of about 45 degrees on the inner surface of the tubes. The bevel provides a relief at the distal ends of the tubes for the flow of the fluid through the tubes and between connections. Thus, the relief is positioned at the open distal ends 28 and 40, at the tee-junction 20, and at the compression fittings on the inlet 36 and the outlet 40 of the measuring device 14.

The operation of the flow controller 10 is discussed with reference to FIGS. 1 and 2. The filter 50 operates to remove particles from the water. As the filter media 54 fills with particles, the outflow of water through the discharge 56 decreases. To maintain flow, the discharge 56 is opened. The increased flow decreases the pressure of the water discharged from the filter. A portion of the water exits the water main 62 through the valve 60 that communicates with the sampling tube 18. The valve 60 is positioned so that a discernable flow of water discharges from the positive-head tube 22 into the catch basin 30. This indicates that the tube 22 is filled with water. The filled tube 22 accordingly is a standpipe having the pressure head H2. The pressure head H2 pushes the sample water through the restriction 12, as discussed below.

A portion of the sample water travels in the inlet tube 34 to the inlet 36 of the measuring device 14. The water passes through the narrow restriction 12 in the measuring device 14 which analyzes the water passing the restriction. For example, known measuring devices direct a light into the fluid. Photosensors measure the reflected light to determine the number and size of the particles in the water. The particular components of the measuring device 14 that evaluate the sample are not illustrated.

The sample water then discharges from the measuring device 14. The water travels through the outlet 42 and the discharge tube 38 to the open distal end 40. The filled portion 44 of the discharge tube 38 creates the negative pressure head H2. This is a suction force on the sample water having the effect of pulling the sample water through the restriction 12.

Changing the length of the portion 44 of the discharge tube 38 affects the flow rate of the fluid through the restriction 12. For example, a shorter portion 44 results in a lower flow rate of fluid. The desired flow rate of fluid through the restriction 12 can thus be set by adjusting the length of the portion 44. A preferred way to adjust the length of the portion 44 is to drill a one-eighth inch hole 74 through the tube as illustrated in FIG. 1. Such a hole spaced about one-half inch 76 from the distal end 40 (or from another such hole) reduces the flow rate by about 5 milliliters per minute. Both the positive head H1 and the negative head H2 combine to provide an effective head that pushes and pulls the fluid at the constant rate through the restriction 12. The ratio of the magnitudes of H1 and H2 is preferably 1:1, but it is preferred that the magnitude of H2 equal or exceed that of H1. A head H2 less than the head H1 will be operative, however.

The length of the positive-head tube 22 and the negative-head portion 44 of the discharge tube 38 is computed by determining the static head sufficient to pass the desired volume of fluid through the restriction. For example, a measuring device has an effective restriction of 0.7 millimeters (0.028 inches) and is designed to measure particles in a sample of fluid traveling at a rate of 100 milliliters per minute (0.0264 gallons per minute). It is noted that the restriction can be an orifice or an elongated restricted area, and can be circular, square, or other shape in cross-section. The measurements are taken during one minute periods, so the total volume of the sample is 100 milliliters. The flow rate (Q) equals the area of the effective restriction (A) times the head pressure (H). $Q = 5.667 \, D^2 \, (H/G_f)^{.5}$ where D is the diameter of the restriction. In this example, the area equals 5.667 (a conversion factor) times the square of 0.028 inches, or 0.0044. The square root of the head pressure H in inches equals the 0.0264 divided by 0.0044, or 35.3077 inches.

The head pressures H1 and H2 are preferably about the same. Accordingly, the portion of the tube 22 above the mean elevation 26 is selected to be 17 inches; the portion 44 is selected to be 18.308 inches. In practice, the portion 44 several inches longer to facilitate any necessary adjustments during installation, as discussed below.

The dual-head flow controller is assembled as discussed above. It is preferred that the discharge tube 38 at installation be longer than computed, so that adjustments to the flow rate can be made during installation. For example, a particular device may have a longer or shorter length of restriction 12, which will affect the flow rate through the restriction. To calibrate the flow controller 10, the flow of water is started by opening the valve 62. The flow should be sufficient to provide a discernable overflow from the positive-head tube 22 into the catch basin 30. The overflow preferably equals the desire flow rate of the fluid through the restriction 12. A graduated cylinder is held under the open end 40 of the discharge tube 38. The cylinder is filled for a one minute period. If the cylinder overflows the mark for the desired volume, the head is too high. In the present example, the cylinder should collect 100 milliliters in the one minute period. To seduce the flow, the lower portion 44 of the discharge tube 38 is shortened. This is preferably accomplished by drilling a one-eighth inch hole through the tube 38 near the distal end 40. Such a hole spaced one half inch from the end 40 will reduce flow by approximately 5 milliliters per minute.

The principles, preferred embodiments, and modes of operation of the present invention have been described in the foregoing specification. The invention is not to be construed as limited to the particular forms disclosed because these are regarded as illustrative rather than restrictive. Moreover, variations and changes may be made by those skilled in the art without departing from the spirit of the invention as described by the following claims.

What is claimed is:

1. A dual-head flow controller for providing a constant rate of fluid flow through a restriction in a measuring chamber for counting particles in the fluid, comprising:
   a supply tube for communicating a fluid from a supply to a restriction in a measuring chamber;
   a positive-head tube having a distal open end and connected for fluid communication with the supply tube and extending a first predetermined distance above a mean elevation of the restriction in the measuring chamber for a pressure head of a first amount;
   a negative-head tube for communicating fluid from the restriction to a distal open end, a portion of the negative-head tube extending downwardly a second distance below the mean elevation of the restriction in the measuring chamber for a pressure head of a second amount,
   wherein the supply tube, the positive-head tube, and the negative-head tube each have a same cross-sectional width of a first value,
   whereby the fluid, being communicated under pressure to the restriction for measuring the particles in the fluid, flows at a constant rate.

2. The dual-head flow controller as recited in claim 1, wherein the restriction has a cross-sectional width of a second value smaller than the first value.

3. The dual-head flow controller as recited in claim 1, further comprising:
   a catch basin connected at a distal end of the positive-head tube for receiving fluid overflow; and
   a drain from the catch basin.

4. The dual-head flow controller as recited in claim 1, wherein the distal ends of the positive-head tube and the negative-head tube each have a positive bevel on an interior surface.

5. The dual-head flow controller as recited in claim 1, wherein the absolute value of the magnitude of the pressure in the negative-head tube is about the same as that in the positive-head tube.

6. The dual-head flow controller as recited in claim 1, wherein the absolute value of the magnitude of the pressure in the negative-head tube is greater than that in the positive-head tube.

7. The dual-head flow controller as recited in claim 1, wherein the absolute value of the magnitude of the pressure in the negative-head tube is less than that in the positive-head tube.

8. A method of supplying a constant rate flow of a fluid to a restriction in a measuring chamber for measuring particles in the fluid, comprising:
   communicating a fluid from a supply to a restriction in a measuring chamber through a positive-head tube having a distal open end with a positive bevel on an interior surface, the positive-head tube extending a first predetermined distance above a mean elevation of the restriction in the measuring chamber for a pressure head of a first amount;
   communicating the fluid through a negative-head tube from the restriction to a distal open end with a positive bevel on an interior surface, a portion of the negative-head tube extending downwardly a second distance below the mean elevation of the restriction in the measuring chamber for a pressure head of a second amount,
   whereby the fluid, being communicated under pressure to the restriction for measuring the particles in the fluid, flows at a constant rate independent of the pressure.

9. A dual-head flow controller for providing a constant rate of fluid flow through a restriction in a measuring chamber for counting particles in the fluid, comprising:
   a supply tube for communicating a fluid from a supply to a restriction in a measuring chamber;
   a positive-head tube having a distal open end with a positive bevel on an interior surface and connected for fluid communication with the supply tube and extending a first predetermined distance above a mean elevation of the restriction in the measuring chamber for a pressure head of a first amount;
   a negative-head tube for communicating fluid from the restriction to a distal open end having a positive bevel on an interior surface, a portion of the negative-head tube extending downwardly a second distance below the mean elevation of the restriction in the measuring chamber for a pressure head of a second amount,
   whereby the fluid, being communicated under pressure to the restriction for measuring the particles in the fluid, flows at a constant rate.

10. The dual-head flow controller as recited in claim 9, wherein the magnitude of the pressure in the negative-head tube is about the same as that inn the positive-head tube.

11. The udal-head flow controller as recited in claim 9, wherein the magnitude of the pressure in the negative-head tube is greater than that in the positive-head tube.

12. The dual-head flow controller as recited cin claim 9, wherein the magnitude of the pressure in the negative-head tube is less than that in the positive-head tube.

* * * * *